United States Patent
Mai et al.

(10) Patent No.: US 9,918,952 B2
(45) Date of Patent: Mar. 20, 2018

(54) POWDEROUS FORMULATION

(71) Applicant: DSM IP ASSETS B.V., Heerlen (NL)

(72) Inventors: Jimbin Mai, Basel (CH); Gang Su, Basel (CH); Pablo Oliver Velarde Pena, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/647,633

(22) PCT Filed: Nov. 28, 2013

(86) PCT No.: PCT/EP2013/075007
§ 371 (c)(1),
(2) Date: May 27, 2015

(87) PCT Pub. No.: WO2014/083124
PCT Pub. Date: Jun. 5, 2014

(65) Prior Publication Data
US 2015/0320714 A1 Nov. 12, 2015

Related U.S. Application Data

(60) Provisional application No. 61/730,636, filed on Nov. 28, 2012.

(51) Int. Cl.
| | |
|---|---|
| *A61K 31/202* | (2006.01) |
| *A61K 9/14* | (2006.01) |
| *A23D 7/005* | (2006.01) |
| *A23D 7/01* | (2006.01) |
| *A23D 9/05* | (2006.01) |

(52) U.S. Cl.
CPC .......... *A61K 31/202* (2013.01); *A23D 7/0053* (2013.01); *A23D 7/011* (2013.01); *A23D 9/05* (2013.01); *A61K 9/145* (2013.01); *A61K 9/146* (2013.01)

(58) Field of Classification Search
CPC ....... A61K 31/202; A61K 9/145; A61K 9/146
See application file for complete search history.

(56) References Cited

U.S. PATENT DOCUMENTS 6,428,832 B2 * 8/2002 Van Den Burg ..... A23C 9/1528
426/302

FOREIGN PATENT DOCUMENTS

| CA | 899 710 | 5/1972 |
|---|---|---|
| EP | 2 181 604 | 5/2010 |
| JP | 2009-505820 | 2/2009 |
| WO | WO 2007/024133 | 3/2007 |
| WO | WO 2010/039036 | 4/2010 |
| WO | WO 2010/149759 | 12/2010 |

OTHER PUBLICATIONS

Typical Fatty-Acid Compositions of Some Common Fats (http://web.pdx.edu/~wamserc/C336S12/fat.pdf ) Jul. 2004.*
Scagneli, "Gluten in Medication", http://www.delightglutenfree.com/gluten-in-medication-understanding-the-risks-and-protecting-yourself1#.VqPWpU2FM-U, Mar. 2012.*
Engineering Toolbox, http://www.engineeringtoolbox.com/particle-sizes-d_934.html, Apr. 2006.*
International Search Report for PCT/EP2013/075007, dated Mar. 27, 2014, 3 pages.
Chapter 2. Standard Tables of Food Composition in Japan, Fifth Revised and Enlarged Edition, 14 Fat and Oils, [online], Jan. 24, 2005 http://www.mext.go.jp/b_menu/shingi/gijyutu/gijyutu3/toushin/05031801/004/013 (2005).
Rodriguez et al, *Novel Ingredient Solutions for Formulating Clear-Type Beverages*, National Starch food Innovation, http://wwwbevindustry.com/ext/resources/White_papers/Q—Naturale-White-Paper.pdf (2011).
Office for Resources, Policy Division Science and Technology Policy Bureau, "Chapter 2.Standard Tables of Food Composition in Japan, Fifth Revised and Enlarged Edition, 10 Fishes and Shellfishes", Jan. 24, 2005.
Notice of Reasons for Rejection, JP Appln No. P2015-543482, dated Sep. 5, 2017.

* cited by examiner

*Primary Examiner* — Sahar Javanmard
(74) *Attorney, Agent, or Firm* — Nixon & Vanderhye P.C.

(57) ABSTRACT

The present invention relates to a powderous formulation comprising powder particles. These powder particles do comprise polyunsaturated oils, especially polyunsaturated fatty acids, and the powder do have at the same time an excellent sensory profile, a fine particle structure and a high oil loading.

5 Claims, No Drawings

POWDEROUS FORMULATION

This application is the U.S. national phase of International Application No. PCT/EP2013/075007 filed 28 Nov. 2013, which designated the U.S. and the benefit of U.S. Provisional Application No. 61/730,636 filed 28 Nov. 2012, the entire contents of each of which are hereby incorporated by reference.

The embodiments of present invention as disclosed herein relate to a powderous formulation comprising powder particles. These powder particles comprise polyunsaturated oils, especially polyunsaturated fatty acids. The powder exhibits at the same time an excellent sensory profile, a fine particle structure and a high oil loading.

During the last years the importance of polyunsaturated oils, especially polyunsaturated fatty acids (PUFAs), have attracted substantial interest as dietary supplements. Today there is reasonable evidence that increasing dietary levels of PUFAs have beneficial effects on health and can reduce the incidence of death from coronary heart diseases via effects on blood pressure, atherosclerosis, and thrombogenesis.

Due to the fact that polyunsaturated oils have more than one carbon-carbon double bond, which are prone to be oxidized. With increasing number of double bonds the polyunsaturated oils are subject to increasing oxidative degradation and development of undesirable "off-flavors", mainly fishy smell and taste. These undesired smells and tastes can be a challenge when these oils have to be incorporated into end-market products.

So there is always a need to provide improved ways how to formulate polyunsaturated oils so that they are stable (against oxidation), also during a longer storage period and they do not have any undesirable "off-flavor".

Surprisingly, it was found that an emulsion comprising
(a) at least one polyunsaturated oil, and
(b) at least one emulsifier, and
(c) at least one carbohydrate with no emulsifying properties, and
(d) optionally at least auxiliary agent, which was dried using supercritical drying conditions had excellent properties in regard to the stability of the polyunsaturated oil.

Therefore some embodiments of the present invention relate to powder particles comprising
(i) an emulsion comprising
  (a) at least one polyunsaturated oil, and
  (b) at least one emulsifier, and
  (c) at least one carbohydrate with no emulsifying properties, and
  (d) optionally at least auxiliary agent, and
(ii) gas cells comprising an inert gas or a mixture of inert gases.

These powder particles (as such as well as in a formulation) are stable and do not have undesired off-flavors.

The powder particles according to the present invention comprise polyunsaturated oil(s) that can be used singly or as a mixture of oils. The polyunsaturated oils are preferably PUFAs. Preferred are the C18-22 PUFAs having 4 carbon-carbon double bonds.

PUFAs are classified according to the position of the double bonds in the carbon chain of the molecule as n-9, n-6 or n-3 PUFAs.

Examples of n-6 PUFAs are linoleic acid (C18:2), arachidonic acid (ARA, C20:4), γ-linolenic acid (GLA, C18:13) and dihomo-γ-linolenic acid (DGLA, C20:3). Examples of n-3 PUFAs are α-linolenic acid (C18:13), eicosapentaenoic acid (EPA, C20:5), and docosahexaenoic acid (DHA, C22:6).

Especially EPA and DHA have attracted interest of the food industry in recent years. The most available sources of these two fatty acids are fish and the marine oils extracted from them.

In one embodiment, the at least one C18-22 PUFA having 4 carbon-carbon double bonds is chosen from docasoahexaenoic acid ("DHA"), eicosapentaenoic acid ("EPA"), arachidonic acid ("ARA"), omega-3 docosapentaenoic acid ("DPA n-3"), and omega-6 docosapentaenoic acid ("DPA n-6"). In some embodiments, the oil comprises omega-3 PUFAs. In further embodiments, the omega-3 PUFAs are chosen from DHA, EPA, DPAn-3, and mixtures thereof.

As stated above the oils can be obtained from various sources including, for example, aquatic animals, such as, fish, marine mammals, and crustaceans (such as krill and other euphausids); animal sources including, for example, animal tissues that include for example brain, liver, and eyes and animal products that include, for example, eggs and milk; microalgae; plant; and/or seed. In one embodiment, the oil is obtained from fish, microalgae, plant or seed.

It is clear that the oils when used in the powder particles can be from a different source even when used in the same powder.

The oil content in the powder is at least 5 weight-% (wt-%), based on the total weight of the powder particles. Preferably, it is more than 10 wt-%.

A preferred range is 5-60 wt-% of at least one polyunsaturated oil, based on the total weight of the powder particles.

The powder particles also comprise at least one emulsifier. A single emulsifier can be used as well as mixture of emulsifiers. The emulsifiers can be carbohydrates, mono-, di-, oligo-, polysaccharides, modified (food) starches. Examples of such emulsifiers are i.e. Q-naturale™ (from National Starch). The emulsifier content is at least 2 wt-%, based on the total weight of the powder particles. A preferred range is 2 45 wt-% of at least one emulsifier, based on the total amount of the powder particles.

Furthermore the powder particles according to the present invention also comprise at least one carbohydrate with no emulsifying properties. A single carbohydrate with no emulsifying properties can be used as well as mixture of carbohydrates with no emulsifying properties. Such carbohydrates with no emulsifying properties are i.e. maltodextrin and/or trehalose. The carbohydrates with no emulsifying properties content is at least 5 wt-%, based on the total weight of the powder particles.

A preferred range is 5-55 wt-% of at least one carbohydrate with no emulsifying properties, based on the total amount of the powder particles.

Furthermore the powder particles can comprise one or more auxiliary agent. Such auxiliary agents can fulfill a wide range of functions. Such auxiliary agents can be used to improve the powder particles and/or the production of the powder particles and/or formulation wherein the powder is incorporated and/or the production of such a formulation. Examples of such auxiliary agents are antioxidants, antimicrobial, pH-buffer, chelating agents, dyes, fillers, etc.

The auxiliary agent content is up to 20 wt-%, based on the total weight of the powder particles.

Furthermore the powder particles comprise gas cells which comprise an inert gas or a mixture of inert gases. These gas cells originate from the supercritical drying process, which is carried out with an inert gas, preferably $CO_2$.

The size of the gas cells (the diameter or in case of non-sperical cell the longest dimension) are usually small in comparison to the size of one powder particle.

The size of the powder particles are in the range of 100-600 nm.

The ratio of size of the gas cells to the size of the particles is at least 1:100.

The powder particles according to the present invention are dried by supercritical drying. The production of the emulsion which is dried afterwards is performed by the usual and commonly known procedures. The supercritical drying is performed according to methods known in the art, such as those evidenced by published International Applications WO 02/102947, WO 2011/134627 and WO 07/024133, the entire contents of each being expressly incorporated hereinto by reference.

Usually the supercritical drying is carried out with $CO_2$ (critical point=304.25 K at 7.39 MPa or 31.1° C. at 1072 psi) or freon (critical point m≈300 K at 3.5-4 MPa or 25-0° C. at 500-600 psi).

The powder particles according to the present invention can be used in any field of application wherein polyunsaturated oils are used. For example, the powder particles can be used in food, feed and/or personal care application. The amount of the powder particles relates to the amount of polyunsaturated oil, which is desired in a specific application.

Therefore a further embodiment of the present invention relates to the use of powder particles (as defined above) in food, feed and/or personal care products.

The products can be in any form (liquid, solid or gel-like). Preferred are products, which are liquid (such as, beverages, especially soft drinks).

Furthermore certain embodiments disclosed herein relate to food, feed and/or personal care products comprising powder particles according to the present invention (as defined above).

The following examples illustrate the present invention.

All the parts and percentages in the Examples are related to the weight (when not otherwise stated) and the temperature is given in ° C. (when not otherwise stated).

EXAMPLES

Example 1

In a first step an emulsion with all the ingredients as listed in table 1 was produced:

TABLE 1

| Ingredients | Wt-% |
| --- | --- |
| Q-Naturale 200, 20-22 brix* | 19.00 |
| Trehalose | 27.90 |
| Sodium Hexametaphosphate | 5.61 |
| Green tea extract (RFI) | 0.79 |
| Sodium Ascorbate | 1.98 |
| NAF B (Ogawa) | 0.40 |
| Sodium succinate | 0.32 |
| DHA S Rosemary Sun 05-6576 (=PUFA) | 19.00 |
| Water DI | 25.00 |

This emulsion was afterwards submitted to the supercritical drying with $CO_2$ according to the techniques disclosed in WO 07/024133.

The average particle size of the particles was 327 nm. The particles exhibited excellent uniformity.

Example 2

In a first step an emulsion with all the ingredients as listed in table 2 was produced:

TABLE 2

| Ingredients | Wt-% |
| --- | --- |
| Q-Naturale 200, 20-22 brix* | 17.70 |
| Maltodextrin | 25.10 |
| Sodium Hexametaphosphate | 5.18 |
| Green tea extract (RFI) | 0.73 |
| Sodium Ascorbate | 1.83 |
| NAF B (Ogawa) | 0.37 |
| Sodium succinate | 0.29 |
| DHA S Rosemary Sun 05-6576 (=PUFA) | 17.70 |
| Water DI | 31.10 |

This emulsion was afterwards submitted to the supercritical drying with $CO_2$ according to the techniques disclosed in WO 07/024133.

The average particle size of the particles was 287 nm. The particles exhibited excellent uniformity.

Example 3

Both powders per Examples 1 and 2 above were incorporated into a grape juice (DHA content 32 mg/serving). No fishy taste was detected.

Example 4

Both powders per Examples 1 and 2 above were incorporated into a Cola beverage (DHA content 32 mg/serving). No fishy taste was detected.

The invention claimed is:

1. A powderous formulation comprising:
   (i) powder particles formed of a supercritical $CO_2$-dried emulsion; and
   (ii) gas cells in the powder particles which comprise $CO_2$ gas, wherein the supercritical $CO_2$-dried particulate emulsion comprises:
      (a) at least one polyunsaturated oil selected from the group consisting of eicosapentaenoic acid (EPA), arachidonic acid (ARA), docosahexaenoic acid (DHA) and docosapentaenoic acid (DPA),
      (b) at least one emulsifier,
      (c) at least one carbohydrate with no emulsifying properties, and
      (d) optionally at least auxiliary agent, and wherein the powder particles have a size in a range of 100 - 600 nm, and the gas cells have a size such that a size ratio of the gas cells to the powder particles is at least 1:100.

2. The powderous formulation according to claim 1, wherein the emulsifier is at least one selected from the group consisting of carbohydrate, mono-polysaccharides, di-polysaccharides, oligo-polysaccharides and modified food starch.

3. The powderous formulation according to claim 1, wherein the auxiliary agent is at least one selected from the group consisting of antioxidants, antimicrobials, pH-buffers, chelating agents, dyes and fillers.

4. The powderous formulation according to according to claim 1, wherein the supercritical $CO_2$-dried emulsion comprises:
   (a) 5 - 60 wt-%, based on the total amount of the powder particles, of the at least one polyunsaturated oil, and (b) 2 - 45 wt-%, based on the total amount of the powder particles, of the at least one emulsifier, and
(c) 5 - 55 wt-%, based on the total amount of the powder particles, of the at least one carbohydrate with no emulsifying properties, and
(d) up to 20 wt-%, based on the total amount of the powder particles, of the at least auxiliary agent.

5. Food products, feed products and/or personal care products comprising the powderous formulation according to claim 1.

\* \* \* \* \*